United States Patent [19]

Kress

[11] Patent Number: 4,554,930
[45] Date of Patent: Nov. 26, 1985

[54] PRESSURE SENSING DEVICE AND METHOD FOR PREVENTING ULCER FORMATION

[76] Inventor: Donald W. Kress, 27 Forest Rd., Wheeling, W. Va. 26003

[21] Appl. No.: 625,651

[22] Filed: Jun. 28, 1984

[51] Int. Cl.$^4$ .............................................. A61B 9/00
[52] U.S. Cl. ..................................... 128/774; 73/172
[58] Field of Search ................ 128/774, 779, 781, 68, 128/68.1, 748; 73/172; 33/174 D; 340/573

[56] References Cited

U.S. PATENT DOCUMENTS 3,974,491  8/1976  Sipe ..................................... 128/779
4,080,653  3/1978  Barnes, Jr. et al. .................. 128/748

OTHER PUBLICATIONS

Book–*Pressure Ulcers,* Edited by M. B. Constantian, Chapters 2 and 3, pp. 7–22.
Article–"The Prevention of Pressure Sores" by R. M. Linder et al., *Surgical Rounds,* Jun. 1983, pp. 42–56.
Article–"An Interface Pressure Sensor for Routine Clinical Use" by J. C. Robertson et al. *Engineering in Medicine,* 1980, pp. 151–156.
Article–"An IC Piezoresistive Pressure Sensor for Biomedical Instrumentation" by Samaun et al., *IEEE Trans. on Biomedical Engin.,* vol. BME-20, Mar. 1973, pp. 101–109.
Article–"Warning Mat to Signal Air Seat Cushion Failure" by Peter Werner et al., *Arch Phys. Med. Rehabil.,* vol. 63, Apr. 1982, pp. 188–190.
Article–"Warning Device for the Prevention of Ischaemic Ulcers in Quadriplegics" by R. Roemer et al., Medical and Biological Engineering, Sep. 1976, pp. 580.
Article–"Warning Device for the Prevention of Ischaemic Ulcers in Patients who have Injured the Spinal Cord" by R. P. Patterson et al., Medical and Biological Engineering, Jul. 1973, pp. 504–505.

*Primary Examiner*—Lee S. Cohen
*Assistant Examiner*—Steven Falk
*Attorney, Agent, or Firm*—Webb, Burden, Robinson & Webb

[57] ABSTRACT

A pressure sensing device includes a sensor for continuously measuring the pressure on a patient's skin at the interface between the skin and a surface exerting pressure on the skin. A monitoring device monitors the pressure exerted on the skin and the elapsed time period during which the skin has been exposed to the measured pressure. An alarm then indicates when the combination of the pressure and the elapsed time is approaching a previously determined level in order to prevent damage to the patient's skin.

17 Claims, 4 Drawing Figures

PRESSURE SENSING DEVICE AND METHOD FOR PREVENTING ULCER FORMATION

BACKGROUND OF THE INVENTION

This invention relates generally to pressure sensing devices for preventing ulcer formation and, more particularly, to a pressure sensing device which continuously measures the pressure between the skin and a surface and indicates when the pressure on the skin should be relieved.

DESCRIPTION OF THE PRIOR ART

Ischaemic ulcers can form on the skin any time that the skin is exposed to excessive pressure for a prolonged period of time. For example, exposure to a pressure of 70 mm Hg for a period of one hour can cause irreversible skin or tissue damage. In addition, there is a possibility of such irreversible skin damage occurring any time that the skin is exposed to pressures of over 30 mm Hg for a prolonged period of time. The known relationship between pressure, elapsed time and skin damage in humans can be expressed in the curve shown in FIG. 1. The formation of ischaemic ulcers is a particular problem for bedridden patients or those confined to a wheelchair such as paraplegics and quadriplegics whose ability to sense and relieve excessive pressure on their skin is restricted.

Various means have been developed to deal with the problem of skin damage due to prolonged exposure to excessive pressure. Werner et al. "Warning Mat to Signal Air Seat Cushion Failure" Arch. Phys. Med. Rehabil. 63:188-190, 1982; Roemer et al. "Warning device for the prevention of ischaemic ulcers in quadriplegics" Med. Biol. Eng. 14:580-581, 1976; and Patterson et al. "Warning device for the prevention of ischaemic ulcers in patients who have injured the spinal cord" Med. Biol. Eng. 11:504-505, 1973 describe warning systems associated with wheelchair seat cushions. All three systems depend in varying degrees on the pressure on the seat and elapsed time and emit a visual and/or audio signal when the pressure on the seat cushion should be relieved. In the Werner et al. system, the pressure on the seat cushion is continuously monitored and a signal is emitted when the pressure reaches a predetermined level. Roemer et al. and Patterson et al. describe systems whereby a signal is emitted periodically to remind the patient to relieve pressure on the seat cushion. The timer is automatically reset when the pressure has been adequately relieved as determined by an absence of pressure registered by the pressure sensor for a predetermined period of time.

One disadvantage of prior art systems is that the actual pressure at the interface between the skin and the surface exerting pressure is not measured and, hence, the actual pressure on the skin, which causes the skin damage, is not known. In addition, the prior art warning systems are not dependent upon both the elapsed time and the pressure to which the skin has been exposed.

It is an object of the present invention to overcome both of these deficiencies in prior art systems and provide a correlation between the actual skin pressure and elapsed time and the warning system.

Pressure sensors have been developed that directly measure the pressure on the skin at the interface between the skin and the surface that is exerting pressure on the skin. Robertson et al. "An interface pressure sensor for routine clinical use" Eng. in Med. 3:151-156, 1980 describes various types of such devices and discusses their use in measuring the pressure on the skin. However, Robertson et al. do not combine the use of such pressure sensors with a continuous monitoring and warning system.

SUMMARY OF THE INVENTION

Accordingly, I have invented a pressure sensing device which includes a sensor for continuously measuring the pressure on a patient's skin at the interface between the skin and a surface exerting pressure on the skin. A microprocessor and a timer monitor the pressure exerted on the skin and the elapsed time period during which the skin has been exposed to the measured pressure. An alarm indicates when the combination of the pressure and the elapsed time is approaching a previously determined level. Each pressure sensor may be in direct contact with the surface of the skin at the interface where the pressure is to be measured or may be implanted just beneath the surface of the skin.

The indication given when the combination of pressure and elapsed time is approaching a previously determined level is preferably an audio signal, although other types of signals may be used such as a visual signal or a combination of a visual and an audio signal. Preferably, the signal is given when the combination of pressure and elapsed time is approaching the level at which irreversible skin damage will occur if the pressure is not relieved.

DETAILED DESCRIPTION OF THE PREFERRED EMBODIMENT

Figure 2:
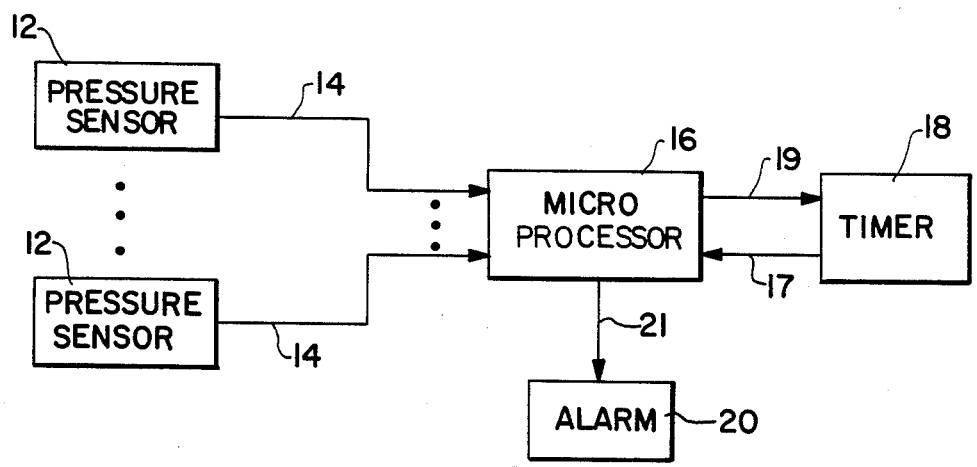
FIG. 2 is a schematic view of the pressure sensing device of the present invention.

A pressure sensing device in accordance with the present invention is shown schematically in FIG. 2. The pressure sensing device includes at least one pressure sensor 12 connected by lead 14 to a microprocessor 16. Pressure sensors 12 may be of any type known in the art that is capable of directly sensing varying pressures within the range of 20 mm Hg to 100 mm Hg. One suitable pressure sensor is described in Samaun et al. "An IC Piezoresistive Pressure Sensor For Biomedical Instrumentation," 20 IEEE Trans. Biomed. Eng. 101-109, 1973, which is incorporated herein by reference.

Figure 1:
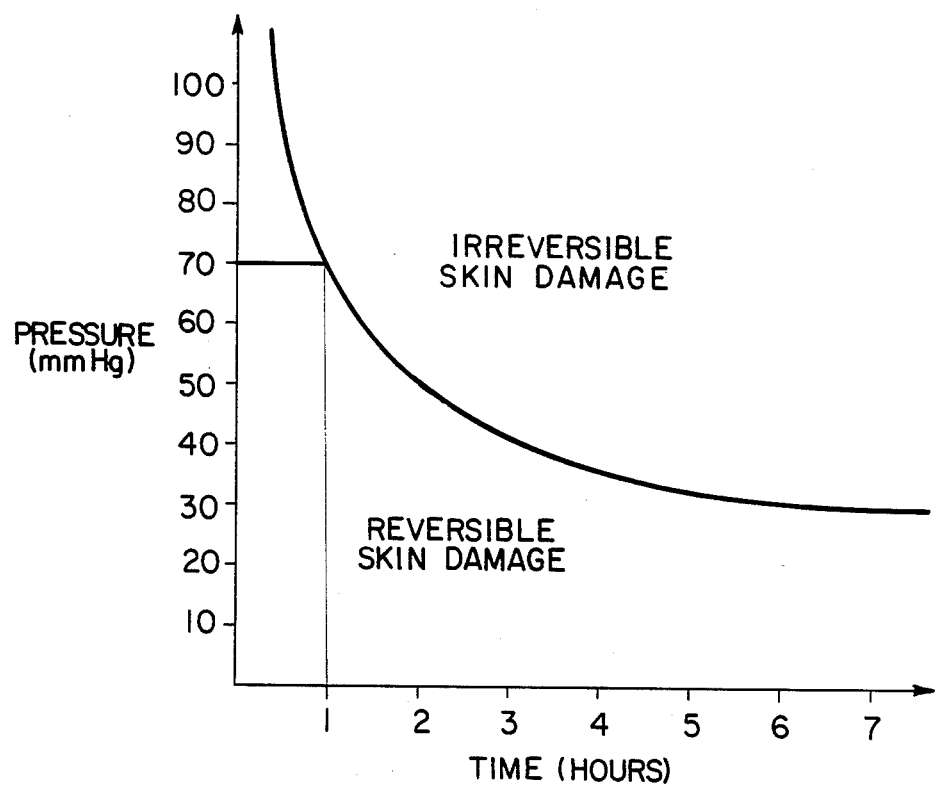
FIG. 1 is a graph showing the relationship between pressure, elapsed time and skin damage.

Microprocessor 16 receives the input from pressure sensors 12 through leads 14. In addition, microprocessor 16 receives an input from a timing device 18 via lead 17 to monitor the elapsed time during which the pressure sensors 12 measured each certain pressure. The timing device 18 is triggered by microprocessor 16 via lead 19 when any of the pressure sensors 12 measure a pressure of 20 mm Hg or more. The combination of measured pressure and the elapsed time is then analyzed by the microprocessor 16 according to the relationship shown in FIG. 1 between the pressure, time and the point where irreversible skin or tissue damage will occur. It is anticipated that the measured pressures will be relatively constant over time because the patients using the invention are not able to shift their own weight without conscious effort.

A signal will be given by alarm 20, as triggered by microprocessor 16 via lead 21, when the point where irreversible skin damage will occur is approached so that the pressure on the skin may be relieved to prevent such skin damage. The signal is preferably an audio signal, but any other type of signal such as a visual signal or a combination of an audio signal and visual signal may be used. Once the warning signal is given, the pressure on the skin should be relieved by the patient. Preferably, the pressure on the affected area is completely relieved for a period of at least one hour.

Figure 3:
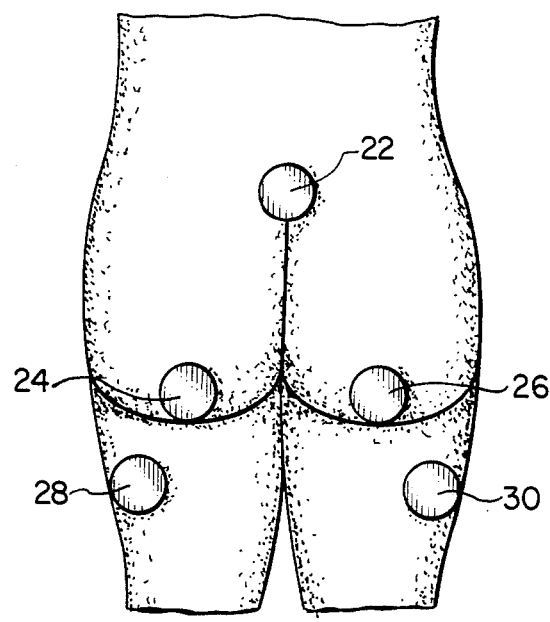
FIG. 3 is a plan view showing the location of pressure sensors on a wheelchair patient.
Figure 4:
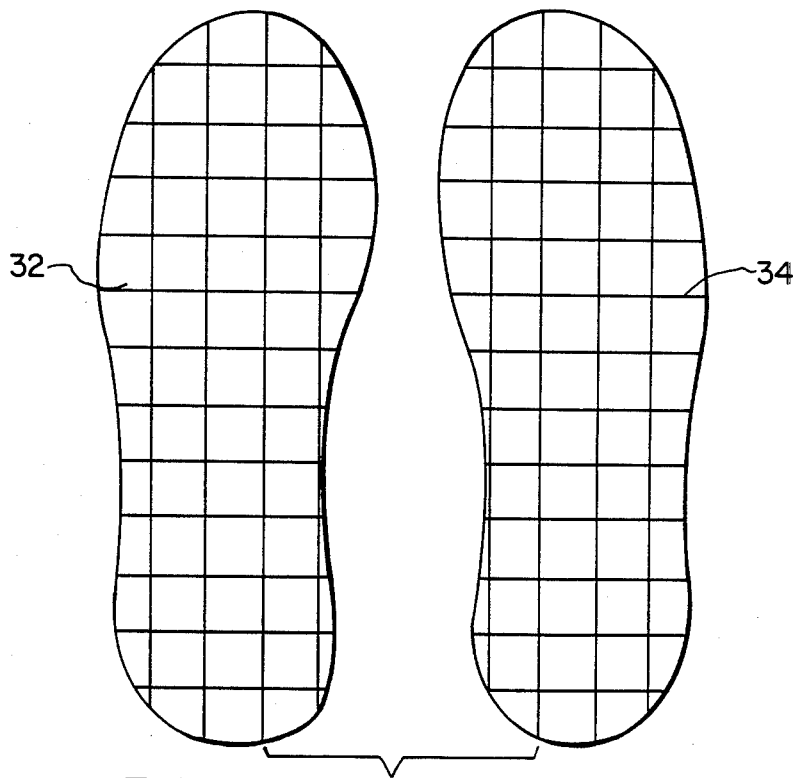
FIG. 4 is a top plan view showing the location of pressure sensors on a grid to be placed in the shoes of patients having neurotropic feet.

Pressure sensors may be externally applied to the skin or implanted just beneath the surface of the skin at any point that is subject to excessive pressure. Typically, these areas will be those having bony protrusions. On patients confined to a wheelchair, for example, the pressure sensors would be placed on the buttocks, one at the sacrum 22, one at each ischium 24 and 26 and one at each trochanter 28 and 30, as shown in FIG. 3. In an alternate embodiment, shown in FIG. 4, the pressure sensors may be on a grid 32 and 34 adapted to be placed in the shoes of patients, such as diabetics, who have neuotropic feet.

Having described a presently preferred embodiment of my invention, it is to be understood that it may otherwise be embodied within the scope of the appended claims.

I claim:

1. A pressure sensing device for monitoring the pressure on a patient's skin in order to prevent damage thereto comprising means for continuously measuring the pressure on the skin at the interface between the skin and a surface exerting the pressure on the skin, means associated with said pressure measuring means for monitoring the pressure exerted on the skin and the elapsed time period during which the skin has been exposed to said measured pressure, and means associated with said monitoring means for indicating when the combination of the pressure measured by said pressure measuring means and the elapsed time is approaching a previously determined level.

2. The pressure sensing device of claim 1 wherein said pressure measuring means includes at least one pressure sensor, each said pressure sensor adapted to be placed in direct contact with the surface of the patient's skin at the interface where the pressure is to be measured.

3. The pressure sensing device of claim 1 wherein said pressure measuring means includes a plurality of pressure sensors adapted to be placed on the surface of the patient's skin at the sacrum, at each ischium, and at each trochanter of the patient.

4. The pressure sensing device of claim 1 wherein said pressure measuring means includes at least one pressure sensor, each said pressure sensor being located on a grid that is adapted to be placed in a shoe.

5. The pressure sensing device of claim 1 wherein said indicating means is a means for generating an audio signal.

6. The pressure sensing device of claim 1 wherein said previously determined level is the combination of measured pressure and elapsed time at which irreversible skin damage will occur if the pressure is not relieved.

7. A method for sensing pressure on a patient's skin to prevent damage thereto comprising the steps of continuously measuring the pressure on the skin at the interface between the skin and a surface exerting the pressure on the skin; monitoring the elapsed time period during which the skin has been exposed to said pressure; and indicating when the combination of the pressure so measured and elasped time is approaching a previously determined level.

8. The method of claim 7 in which said pressure is measured by at least one pressure sensor placed in direct contact with the surface of the patient's skin at the interface where the pressure is to be measured.

9. The method of claim 8 in which pressure sensors are placed on the skin of the patient at the sacrum, at each ischium and at each trochanter.

10. The method of claim 7 in which said pressure is measured by pressure sensors located on a grid that is adapted to be placed in a shoe.

11. The method of claim 7 wherein an audio signal indicates when the combination of the pressure so measured and elapsed time is approaching said previously determined level.

12. The method of claim 7 in which said previously determined combination of measured pressure and elapsed time is the level at which irreversible tissue damage will occur if the pressure is not relieved.

13. A method for preventing tissue destruction caused by excessive pressure on a patient's skin comprising the steps of continuously measuring the pressure on the skin at the interface between the skin and a surface exerting the pressure on the skin; monitoring the elapsed time period during which the skin has been exposed to said pressure; indicating when the combination of the pressure so measured and elapsed time is approaching the level at which irreversible tissue damage will occur if the the pressure is not relieved; and relieving the pressure on the skin when the level at which irreversible tissue damage will occur if the pressure is not relieved is reached.

14. The method of claim 13 in which said pressure is measured by at least one pressure sensor placed in direct contact with the surface of the skin at the interface where the pressure is to be measured.

15. The method of claim 14 in which pressure sensors are placed on the skin of the patient at the sacrum, at each ischium and at each trochanter.

16. The method of claim 13 in which in which said pressure is measured by pressure sensors located on a grid that is adapted to be placed in a shoe.

17. The method of claim 13 wherein an audio signal indicates when the combination of the pressure so measured and elapsed time is approaching the level at which irreversible tissue damage will occur if the pressure is not relieved.

* * * * *